United States Patent [19]

Lal et al.

[11] Patent Number: 4,482,556

[45] Date of Patent: Nov. 13, 1984

[54] PYRIMIDO (6,1-a)ISOQUINOLIN-4-ONE DERIVATIVES

[75] Inventors: Bansi Lal; Horst Dornauer; Bani K. Bhattacharya; Alihussein N. Dohadwalla; Noel J. de Souza, all of Bombay, India

[73] Assignee: Hoechst Aktiengesellschaft, Frankfurt am Main, Fed. Rep. of Germany

[21] Appl. No.: 134,080

[22] Filed: Mar. 26, 1980

Related U.S. Application Data

[63] Continuation-in-part of Ser. No. 848,289, Nov. 3, 1977, abandoned.

[30] Foreign Application Priority Data

May 5, 1977 [DE] Fed. Rep. of Germany ....... 2720085

[51] Int. Cl.$^3$ .................. A61K 31/505; C07D 471/04
[52] U.S. Cl. ................................. 424/251; 424/248.4; 544/115; 544/244; 544/247; 544/252; 546/146
[58] Field of Search ............... 544/252, 244, 247, 115; 424/251, 248.4

[56] References Cited

U.S. PATENT DOCUMENTS 3,021,331  2/1962  Lombardino et al. .............. 544/252
3,081,306  3/1963  Lombardino et al. .............. 544/252

OTHER PUBLICATIONS

Lal et al., "Chemical Abstracts", vol. 90, 1979, col. 90:54969z.
Lal et al., "Chemical Abstracts", vol. 90, 1979, col. 90:54974y.
Lal et al., "Chemical Abstracts", vol. 91, 1979, col. 91:39527f.

*Primary Examiner*—Glennon H. Hollrah
*Assistant Examiner*—James H. Turnipseed
*Attorney, Agent, or Firm*—Curtis, Morris & Safford

[57] ABSTRACT

What are disclosed are pyrimido (6,1-a)isoquinolin-4-one compounds useful as hypotensive agents, bronchodilators, and anti-allergenics, intermediates useful in their preparation, and methods for making the compounds and intermediates.

13 Claims, No Drawings

PYRIMIDO (6,1-A)ISOQUINOLIN-4-ONE DERIVATIVES

This application is a continuation-in-part application of application Ser. No. 848,289 filed Nov. 3, 1977 and now abandoned.

This invention relates to a novel class of pyrimido(6,1-a)isoquinolin-4-one derivatives, to new intermediates used in their preparation and to processes for the preparation of the intermediates and the compounds of the invention. The pyrimido(6,1-a)isoquinolin-4-one derivatives of the invention possess valuable pharmacological properties, for example blood pressure lowering properties as demonstrated in cats and dogs, bronchodilatory properties as demonstrated by antagonism to histamine-induced bronchoconstriction in guinea pigs and anti-allergic properties as demonstrated by the inhibition of passive cutaneous anaphylaxis (pca) in rats.

The invention, therefore, provides pyrimido(6,1-a)isoquinolin-4-one derivatives bearing a novel heterocyclic ring system of the formula I

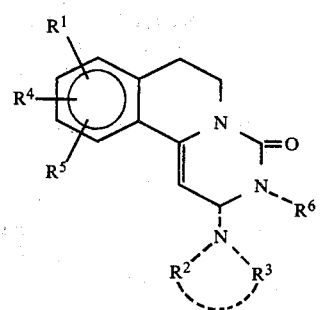

in which
$R^1$, $R^4$ and $R^5$, which may be the same or different, stand for hydrogen, hydroxy, $C_1$–$C_3$-alkoxy, dialkylphosphinylalkoxy, acyloxy or halogen,
two of the radicals $R^1$, $R^4$ or $R^5$, when in adjacent positions and taken together, may form a methylenedioxy or an ethylenedioxy group,
$R^2$ and $R^3$, which may be the same or different, stand for hydrogen, hydroxy, $C_1$–$C_3$-alkoxy, amino, alkylamino, dialkylamino, arylamino, amino or alkyl substituted by a 5- or 6-membered carbon ring containing up to 3 hetero atoms selected from the group of N, O, and S, alkyl, cycloalkyl, hydroxyalkyl, alkoxyalkyl, dialkoxyalkyl, haloalkyl, dialkylaminoalkyl, aralkyl, acyl and optionally substituted aryl, aryl denoting an aromatic hydrocarbon radical having up to 10 carbon atoms;
$R^2$ represents a pair of electrons if $R^6$ stands for one of the radicals defined below and
$R^2$ and $R^3$ when taken together with the nitrogen atom to which they are bound may form an optionally substituted nitrogen heterocycle possibly containing a further nitrogen or oxygen atom, and
$R^6$ stands for hydrogen, alkyl, cycloalkyl, hydroxyalkyl, alkoxyalkyl, dialkoxyalkyl, haloalkyl, dialkylaminoalkyl, aralkyl, heterocyclically substituted alkyl, dialkylphosphinylalkyl, acyl and optionally substituted aryl or
$R^6$ represents a pair of electrons if $R^2$ represents one of the radicals defined above;
and the acid addition salts and quaternary ammonium salts thereof.

In the case of at least one of the two radicals $R^2$ and $R^3$ being hydrogen, the above definition of the pyrimido(6,1-a)isoquinolin-4-one derivatives also encompasses the isomers of the following formula Ib, obtained by complete isomerization of compounds of formula Ia or being in equilibrium with the compounds of formula Ia.

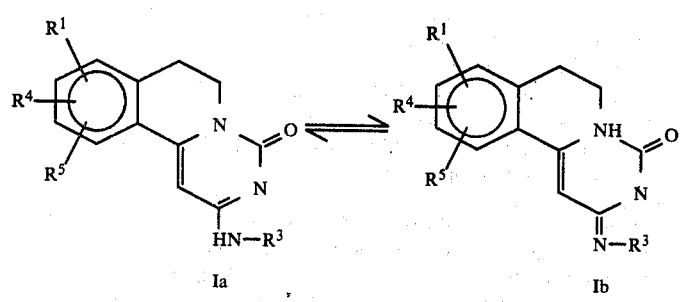

The definition of the pyrimido(6,1-a)isoquinolin-4-one derivatives also encompasses the isomer of formula IC

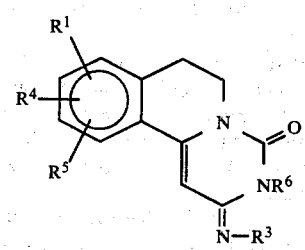

in which $R^1$, $R^3$, $R^4$ $R^5$ and $R^6$ have the above meanings.

Suitable acyloxy radicals for $R^1$, $R^4$ or $R^5$ are those in which the acyl group is linear or branched $C_1$–$C_6$ alkanoyl, for example acetyl, or aroyl, especially benzoyl in which the phenyl nucleus may be substituted one to three times by halogen, nitro, hydroxy, $C_1$–$C_3$ alkoxy and $C_1$–$C_3$ alkyl.

If $R^1$, $R^4$, or $R^5$ stand for halogen, chlorine is preferred.

Suitable dialkylphosphinylalkoxy radicals for $R^1$, $R^4$ or $R^5$ are those in which the alkyl and alkoxy groups carry at most 3 carbon atoms, for example dimethylphosphinylmethoxy.

Especially suitable alkylamino or dialkylamino radicals for $R^2$ or $R^3$ are those in which the alkyl groups have at most 3 carbon atoms, for example methylamino or dimethylamino.

Suitable arylamino radicals for $R^2$ or $R^3$ are phenylamino radicals in which the phenyl residue may be substituted one or several times by halogen, for example chlorine, $C_1$–$C_3$ alkyl, for example methyl, or nitro. A suitable nitrogen-containing heterocyclic amino radical for R² or R³ is, for example, the N-morpholinoamino radical.

As alkyl radical for R², R³ or R⁶ there can be used those having at most 6 carbon atoms, for example methyl, ethyl, n-propyl, isopropyl, butyl, isobutyl, sec.-butyl, or tert.butyl.

Suitable cycloalkyl radicals for R², R³ and R⁶ are those having at most 6 carbon atoms, for example cyclohexyl.

If R², R³, or R⁶ are substituted alkyl, they may be alkyl having up to 6 carbon atoms and substituted by one or two hydroxy or $C_1$–$C_3$ alkoxy groups, halogen atoms, for example chlorine, amino or di($C_1$–$C_4$ alkyl)amino, dialkylphosphinylalkyl, for example dimethylphosphinylmethyl.

Examples of aralkyl radicals for R², R³ and R⁶ are those having at most 8 carbon atoms, in which the aryl radical may be mono- or polysubstituted, especially substituted one, two, or three times by the substituents defined above for R¹.

Suitable heterocyclic alkyl radicals for R², R³ and R⁶ are, for example, furfuryl and tetrahydrofurfuryl.

Suitable examples of aryl radicals for R², R³ and R⁶ are phenyl radicals optionally substituted one or several times, preferably one, two or three times by halogen, for example fluorine, chlorine and bromine, $C_1$–$C_3$ alkyl and $C_1$–$C_3$ alkoxy, for example methyl, ethyl, methoxy and ethoxy, haloalkyl, for example trifluoromethyl, amino or hydroxy, in the latter the hydrogen atoms possibly being replaced by an alkali metal, for example sodium.

Suitable nitrogen-containing heterocyclic radicals are, for example, pyrrolidino, piperidino, morpholino, and piperazino, optionally substituted by alkyl, alkoxycarbonyl, aryl or a nitrogen heterocycle, the terms alkyl, alkoxy, aryl and nitrogen heterocycle having the above meaning.

Examples of suitable acyl radicals for R², R³ and R⁶ are linear or branched $C_1$–$C_6$ alkanoyl, such as acetyl, or aroyl, such as benzoyl, wherein the phenyl residue may be substituted one or several times by the substituents defined above for R², R³ and R⁶ when they represent an aryl radical.

As salts of the pyrimido(6,1-a)isoquinolin-4-one derivatives of the invention, salts of inorganic or organic acids, for example the hydrochlorides, hydrobromides, sulfates, phosphates, acetates, oxalates, tartrates, citrates, maleates, or fumarates are mentioned by way of example.

Suitable quaternary ammonium salts of the pyrimido(6,1-a)isoquinolin-4-one derivatives of the invention are, for example, the salts derived from alkyl halides, such as methiodides.

Preferred substitutents are:
alkoxy for R¹ and R⁴, hydrogen for R⁵,
$C_1$–$C_6$ alkyl or phenyl optionally substituted one to three times as defined above for R²,
hydrogen, $C_1$–$C_6$ alkyl, cycloalkyl, substituted alkyl, aralkyl, heterocyclic alkyl, substituted aryl and $C_1$–$C_6$ alkanoyl for R³ and R⁶.

Particularly preferred compounds of the invention are:
9,10-dimethoxy-2-tert-butylamino-6,7-dihydro-4H-pyrimido(6,1-a)isoquinolin-4-one hydrochloride,
9,10-dimethoxy-2-sec-butylamino-6,7-dihydro-4H-pyrimido(6,1-a)isoquinolin-4-one hydrochloride,
9,10-dimethoxy-2-(2,6-dimethylanilino)-6,7-dihydro-4H-pyrimido(6,1-a)isoquinolin-4-one,
9,10-dimethoxy-2-(2,4-dimethylanilino)-6,7-dihydro-4H-pyrimido(6,1-a)isoquinolin-4-one,
9,10-dimethoxy-2-(2-chloroanilino)-6,7-dihydro-4H-pyrimido(6,1-a)isoquinolin-4-one hydrochloride monohydrate,
9,10-dimethoxy-2-(2,4,6-trimethylanilino)-6,7-dihydro-4H-pyrimido(6,1-a)isoquinolin-4-one hydrochloride dihydrate,
9,10-dimethoxy-3-methyl-2-mesitylimino-2,3,6,7-tetrahydro-4H-pyrimido(6,1-a)isoquinolin-4-one hydrochloride,
9,10-dimethoxy-2-(N-methyl-2,4,6-trimethylanilino)-6,7-dihydro-4H-pyrimido(6,1-a)isoquinolin-4-one hydrochloride,
9,10-dimethoxy-2-(N-isopropyl-2,4,6-trimethylanilino)-6,7-dihydro-4H-pyrimido(6,1-a)isoquinolin-4-one,
9,10-dimethoxy-3-isopropyl-2-mesitylimino-2,3,6,7-tetrahydro-4H-pyrimido(6,1-a)isoquinolin-4-one,
9,10-dimethoxy-2-(N-ethyl-2,4,6-trimethylanilino)-6,7-dihydro-4H-pyrimido(6,1-a)isoquinolin-4-one,
9,10-dimethoxy-3-ethyl-2-mesitylimino-2,3,6,7-tetrahydro-4H-pyrimido(6,1-a)-isoquinolin-4-one,
9,10-dimethoxy-2-(N-acetyl-2,4,6-trimethylanilino)-6,7-dihydro-4H-pyrimido(6,1-a)isoquinolin-4-one.

In the following Table I there are listed some of the new pyrimido(6,1-a)isoquinolin-4-one derivatives.

TABLE I

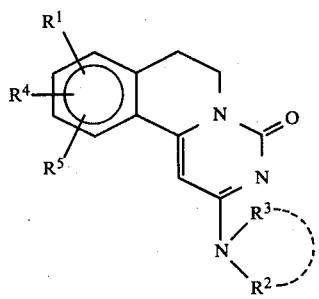

| R⁵ | R¹ + R⁴ | R² | R³ | melting point of the free base (°C.) | Salt | melting point of salt (°C.) |
|---|---|---|---|---|---|---|
| H | 9,10(OCH₃)₂ | H | H | — | HCl | 300 |
| H | 9,10(OCH₃)₂ | H | OH | — | HCl | 264–266 |
| H | 9,10(OCH₃)₂ | H | NH₂ | — | HCl | 236–238 |

TABLE I-continued

| R⁵ | R¹ + R⁴ | R² | R³ | melting point of the free base (°C.) | Salt | melting point of salt (°C.) |
|---|---|---|---|---|---|---|
| H | 9,10(OCH₃)₂ | H |  | — | HCl.½H₂O | 251 |
| 11-OCH₃ | 9,10(OCH₃)₂ | H | 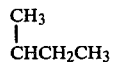 | 239–241 | — | — |
| H | 9,10(OCH₃)₂ | H | CH₃ | — | 2HCl.H₂O | 179–181 (decomp.) |
| H | 9,10(OCH₃)₂ | H | CH₂CH₂CH₃ | — | HCl | 204–207 |
| H | 9,10(OCH₃)₂ | H | CH₂CH₂CH₃ | 173–175 | — | — |
| H | 2H | H | CH₂CH₂CH₂CH₃ | — | HCl | 235–237 |
| H | 9,10(OCH₃)₂ | H | CH₂CH₂CH₂CH₃ | 184–190 | — | — |
| H | 9,10(OCH₃)₂ | CH₃ | CH₃ | — | HCl | 180–181 |
| H | 9,10(OCH₃)₂ | CH₂CH₃ | CH₂CH₃ | 219–220 | — | — |
| H | 9,10(OCH₃)₂ | CH₂CH₂CH₃ | CH₂CH₂CH₃ | 67–69 | — | — |
| H | 9,10(OH)₂ | CH₂CH₂CH₃ | CH₂CH₂CH₃ | 293–295 | — | — |
| H | 9,10(OCH₃)₂ | H | CH(CH₃)₂ | — | HCl | 230–233 |
| H | 9,10(OCH₃)₂ | H | CH₂CH(CH₃)₂ | 157–160 | — | — |
| H | 9,10(OCH₃)₂ | H | CH₃<br>\|<br>CHCH₂CH₃ | — | HCl.H₂O | 218–225 (decomp.) |
| H | 2H | H | CH₃<br>\|<br>CHCH₂CH₃ | — | HCl | 133–135 |
| H | 9,10(OH)₂ | H | CH₃<br>\|<br>CHCH₂CH₃ | — | HCl | 290–300 |
| 11-OCH₃ | 9,10(OCH₃)₂ | H | CH₃<br>\|<br>CHCH₂CH₃ | — | HCl | 193–195 |
| H | 9,10(OH)₂ | H | CH₂CH(CH₃)₂ | 305–315 (decomp.) | — | — |
| H | 9,10(OCH₃)₂ | H | C(CH₃)₃ | — | HCl | 265–270 |
| 11-OCH₃ | 9,10(OCH₃)₂ | H | C(CH₃)₃ | — | HCl | 222–224 |
| H | 2H | H | C(CH₃)₃ | — | HCl | 205–206 |
| H | 9,10(OCH₃)₂ | H | CH₂CH₂N(C₂H₅)₂ | — | 2HCl.H₂O | 147–150 |
| H | 9,10(OCH₃)₂ | H | CH₂CH₂Cl | — | HCl | 246–248 (decomp.) |
| H | 9,10(OCH₃)₂ | H | CH₂CH₂OH | 203–204 | — | — |
| H | 2H | H | CH₂CH₂OH | — | HCl | 230–231 |
| H | 2H | H | CH₂CH₂CH(OMe)₂ | 154–155 | — | — |
| H | 9,10(OCH₃)₂ | CH₃ | 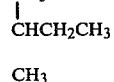 | 166–167 | — | — |
| H | 9,10(OCH₃)₂ | H | 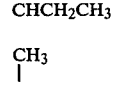 | 237–239 | — | — |
| H | 9,10(OCH₃)₂ | H | 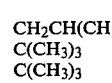 | — | HCl | 199–201 |

TABLE I-continued

| R⁵ | R¹ + R⁴ | R² | R³ | melting point of the free base (°C.) | Salt | melting point of salt (°C.) |
|---|---|---|---|---|---|---|
| H | 9,10(OCH₃)₂ | H | CH₂-(2-furyl) | 217–218 | — | — |
| H | 9,10(OCH₃)₂ | H | CH₂CH₂-(3,4-dimethoxyphenyl) | 179–180 | — | — |
| H | 9,10(OCH₃)₂ | H | CH₂CH₂-(3,4,5-trimethoxyphenyl) | 178–180 | — | — |
| H | 9,10(OCH₃H₃)₂ | | cyclohexyl | — | HCl | 233–236 |
| H | 9,10(OCH₃)₂ | | tetrahydropyran-4-yl | — | HCl | 233–237 |
| H | 9,10(OCH₃)₂ | | N-COOEt piperidinyl | 183–184 | — | — |
| H | 9,10(OCH₃)₂ | | N-CH₃ piperidinyl | — | HCl | 260–263 |
| H | 9,10(OCH₃)₂ | | 1-piperidinyl-cyclohexyl | — | 2HCl | 215–218 |
| H | 9,10(OCH₃)₂ | | N-(4-methoxyphenyl)piperidinyl | — | HCl | 153–155 |

TABLE I-continued

| $R^5$ | $R^1 + R^4$ | $R^2$ | $R^3$ | melting point of the free base (°C.) | Salt | melting point of salt (°C.) |
|---|---|---|---|---|---|---|
| H | 9,10(OCH$_3$)$_2$ | | piperidinyl-phenyl-CF$_3$ (3-CF$_3$) | 220 | — | — |
| H | 9,10(OCH$_3$)$_2$ | H | phenyl | 303–305 | — | — |
| H | 9,10(OCH$_3$)$_2$ | H | 3-CF$_3$-phenyl | 301–302 | — | — |
| H | 9,10(OCH$_3$)$_2$ | H | 2,5-(CH$_3$O)$_2$-phenyl | 268–269 | — | — |
| H | 9,10(OCH$_3$)$_2$ | H | 2,4-(CH$_3$)$_2$-phenyl | 303–305 | — | — |
| H | 9,10(OCH$_3$)$_2$ | H | 4-Cl-phenyl | 294–295 | — | — |
| H | 9,10(OCH$_3$)$_2$ | H | 2,6-(CH$_3$)$_2$-phenyl | 297–299 | — | — |
| H | 9,10(OCH$_3$)$_2$ | H | 4-OEt-phenyl | 272–274 | — | — |

TABLE I-continued
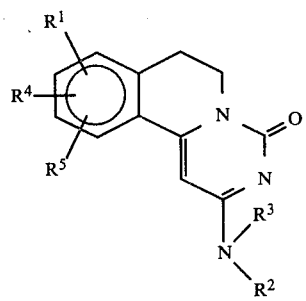
| $R^5$ | $R^1 + R^4$ | $R^2$ | $R^3$ | melting point of the free base (°C.) | Salt | melting point of salt (°C.) |
|---|---|---|---|---|---|---|
| H | 9,10(OCH$_3$)$_2$ | H | 2,5-(CH$_3$)$_2$-C$_6$H$_3$ | 285–287 | — | — |
| H | 2H | H | 2,4-(CH$_3$)$_2$-C$_6$H$_3$ | 278–279 | — | — |
| H | 9,10(OCH$_3$)$_2$ | H | 2,5-(CH$_3$)$_2$-C$_6$H$_3$ | 239–241 | — | — |
| 11-OCH$_3$ | 9,10(OCH$_3$)$_2$ | H | 2,5-(CH$_3$)$_2$-C$_6$H$_3$ | 222–225 | — | — |
| H | 9,10(OCH$_3$)$_2$ | H | 4-ONa-C$_6$H$_4$ | 300 | — | — |
| H | 9,10(OCH$_3$)$_2$ | H | 2,4-Cl$_2$-C$_6$H$_3$ | 274–276 | — | — |
| H | 9,10(OCH$_3$)$_2$ | H | 2-EtO-C$_6$H$_4$ | — | HCl | 185–187 |
| H | 9,10(OCH$_3$)$_2$ | H | 2-Et-C$_6$H$_4$ | 250–251 | — | — |

TABLE I-continued

| $R^5$ | $R^1 + R^4$ | $R^2$ | $R^3$ | melting point of the free base (°C.) | Salt | melting point of salt (°C.) |
|---|---|---|---|---|---|---|
| H | 9,10-O(CH$_2$)$_2$O | H | 2-Et-phenyl | 235–238 | — | — |
| H | 9,10-O(CH$_2$)$_2$O | CH$_2$CH$_2$OH | 2-Et-phenyl | 184–186 | — | — |
| H | 9,10(OCH$_3$)$_2$ | H | 2-Cl-phenyl | — | HCl.H$_2$O | 182–186 |
| H | 9,10(OCH$_3$)$_2$ | H | 2-CH$_3$-3,4-diCl-phenyl | — | 2HCl | 199–203 |
| H | 9,10(OPr)$_2$ | CH$_2$CH$_2$CH$_3$ | CH$_2$CH$_2$CH$_3$ | 73–75 | — | — |
| H | 9,10(OCH$_2$O) | CH$_2$CH$_2$CH$_3$ | CH$_2$CH$_2$CH$_3$ | 228–230 | — | — |
| H | 9,10(OCOCH$_3$)$_2$ | CH$_2$CH$_2$CH$_3$ | CH$_2$CH$_2$CH$_3$ | 101–103 | — | — |
| H | 9,10(OCH$_3$)$_2$ | H | 2,3-diCl-phenyl | 228–230 | — | — |
| H | 9,10(OH)$_2$ | H | 2-Et-phenyl | — | HCl | 293–295 |
| H | 9,10(OCH$_3$)$_2$ | H | 2,3-diOCH$_3$-phenyl | — | HCl.H$_2$O | 238–241 |

TABLE I-continued
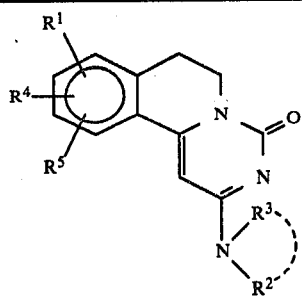
| $R^5$ | $R^1 + R^4$ | $R^2$ | $R^3$ | melting point of the free base (°C.) | Salt | melting point of salt (°C.) |
|---|---|---|---|---|---|---|
| H | 9,10(OCH$_3$)$_2$ | H | 3,4,5-tri(OCH$_3$)-phenyl | — | HCl.H$_2$O | 295–297 |
| H | 9,10(OCH$_3$)$_2$ | H | 3,4,5-tri(CH$_3$)-phenyl | — | HCl.2H$_2$O | 167–169 |
| H | 9,10(OCH$_3$)$_2$ | —CH(CH$_3$)$_2$ | 3,4,5-tri(CH$_3$)-phenyl | 182–183 | — | — |
| H | 9,10(OCH$_3$)$_2$ | CH$_3$ | 3,4,5-tri(CH$_3$)-phenyl | — | HCl | 189–191 (decomp.) |
| H | 9,10(OCH$_3$)$_2$ | —(CH$_2$)$_3$—CH$_3$ | 2,4,6-tri(CH$_3$)-phenyl | 177–178° | — | — |
| H | 9,10(OCH$_3$)$_2$ | —CH$_2$—CH$_3$ | 2,4,6-tri(CH$_3$)-phenyl | 164–165° | — | — |
| H | 9,10(OCH$_3$)$_2$ | —COCH$_3$ | 2,4,6-tri(CH$_3$)-phenyl | 210–212° | — | — |

In the following table Ia are listed pyrimido(6,1-a)isoquinolin-4-one derivatives according to the invention the structure of which corresponds to that of isomer Ic. The melting points of the free bases or of the salts are likewise indicated.

TABLE Ia

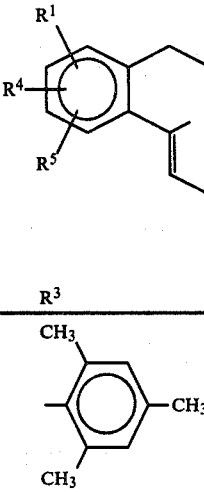

| $R^5$ | $R^1 + R^4$ | $R^6$ | $R^3$ | melting point of the free bases (°C.) | Salt | melting point of salt (°C.) |
|---|---|---|---|---|---|---|
| H | 9,10(OCH$_3$)$_2$ | —CH$_3$ | 2,4,6-tri-CH$_3$-phenyl | 151–152 | HCl<br>CH$_3$I | 198–200<br>221–222 |
| H | 9,10(OCH$_3$)$_2$ | —CH(CH$_3$)$_2$ | 2,4,6-tri-CH$_3$-phenyl | 178–179 | — | — |
| H | 9,10(OCH$_3$)$_2$ | —CH$_2$P(CH$_3$)$_2$ (=O) | 2,4,6-tri-CH$_3$-phenyl | — | HCl | 208–211 |
| H | 9,10(OCH$_3$)$_2$ | —C(=O)CH$_3$ | 2,4,6-tri-CH$_3$-phenyl | 210–212 | — | — |
| H | 9,10(OCH$_3$)$_2$ | —CH$_3$ | 2,4-di-CH$_3$-phenyl | — | HCl | 202–203 |
| H | 9,10(OCH$_3$)$_2$ | —CH$_3$ | 2,4-di-CH$_3$-phenyl | — | HCl | 203–206 (decomp.) |
| H | 9,10(OCH$_3$)$_2$ | —CH$_2$—CH$_3$ | 2,4,6-tri-CH$_3$-phenyl | 142–143 | — | — |

TABLE Ia-continued

| $R^5$ | $R^1 + R^4$ | $R^6$ | $R^3$ | melting point of the free bases (°C.) | Salt | melting point of salt (°C.) |
|---|---|---|---|---|---|---|
| H | 9,10(OCH$_3$)$_2$ | —CH$_2$—CH(CH$_3$)—CH$_2$NMe$_2$ | 3,5-(CH$_3$)$_2$-C$_6$H$_3$ | 145–146 | — | — |
| H | 9,10(OCH$_3$)$_2$ | CH$_3$ | -n-(CH$_2$)$_3$—CH$_3$ | 120–121 | — | — |

It is another object of the present invention to provide novel intermediates and their salts suitable for the preparation of the pyrimido(6,1-a)isoquinolin-4-one derivatives of the invention. The novel intermediates correspond to the formulae III and IV

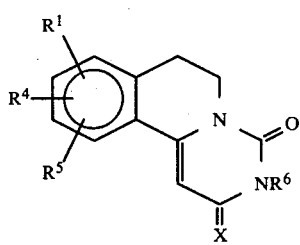

III

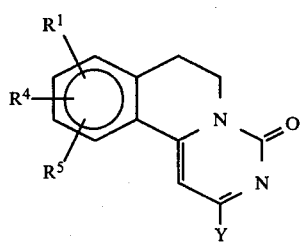

IV in which
R$^1$, R$^4$, R$^5$ and R$^6$ have the above meaning,
X is oxygen or sulfur and
Y is halogen, for example chlorine; alkoxy or alkylthio, alkoxy and alkyl having the meaning as defined earlier in this text, with the exception of the compound of formula III in which R$^1$, R$^6$, R$^4$ and R$^5$ are hydrogen and X is oxygen or sulfur [cf. L. Capuano and K. Mueller, Chem.Ber. 108, 1541 (1975)].

The intermediates of formulae III and IV are listed in Table II which also includes the melting poits of these compounds.

TABLE II

| $R^1 + R^4$ | $R^5$ | $R^6$ | X | Y | melting point (°C.) |
|---|---|---|---|---|---|
| 2H | H | H | O | — | 260° C. |
| 2H | H | H | S | — |  |
| 2H | H | — | — | Cl | 179–180° |

TABLE II-continued

| $R^1 + R^4$ | $R^5$ | $R^6$ | X | Y | melting point (°C.) |
|---|---|---|---|---|---|
| 9,10(OCH$_3$)$_2$ | H | H | O | — | 323–325° |
| 9,10(OCH$_3$)$_2$ | H | H | S | — | 236–237° |
| 9,10(OCH$_3$)$_2$ | H | — | — | SCH$_3$ | 203–205° |
| 9,10(OCH$_3$)$_2$ | H | — | — | Cl | 235–236° |
| 9,10(OCH$_3$)$_2$ | H | — | — | OBu | 158–159° |
| 9,10(OH)$_2$ | H | H | O | — | >260° |
| 9,10(OCH$_3$)$_2$ | 11-OCH$_3$ | H | O | — | 215—218° |
| 9,10(OCH$_3$)$_2$ | 11-OCH$_3$ | — | — | Cl | 176–178° |
| H, 10-Cl | H | H | O | — | >250° |
| H, 10-Cl | H | — | — | Cl | >250° |
| 9,10(OCH$_3$)$_2$ | H | CH$_3$ | O | — | 260–262° |
| 9,10(OCH$_3$)$_2$ | H | CH$_3$ | S | — | 230–231° |
| 9,10(OCH$_3$)$_2$ | H | CH(CH$_3$)$_2$ | O | — | 190–192° |

It is another object of the present invention to provide a process for the preparation of the intermediates of formula III in which X is oxygen, which comprises reacting a compound of formula V

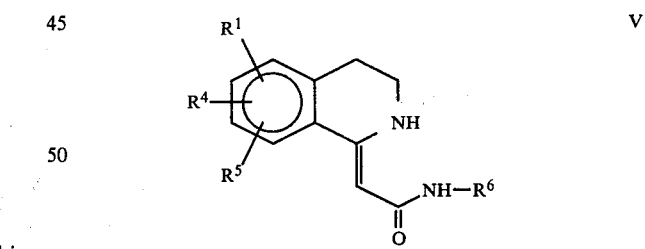

V in which R$^1$, R$^4$, R$^5$ and R$^6$ have the aforesaid meaning with a compound of the formula

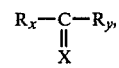

in which
X is oxygen,
R$_x$=R$_y$ is NH$_2$, Cl, or alkoxy, or
R$_x$ is alkoxy and R$_y$ is Cl
using known methods [cf. Shaw & Wooley, J.Biol.-Chem. 181, 89 (1949); A. Dornow & D. Wille, Chem.Ber. 98; 1505 (1965)]. As an alkyl haloformate, ethylchloroformate may be used and, as a dialkyl carbonate, diethyl carbonate may be used. Suitable bases are alkali metal alkoxides, for example sodium methylate, sodium ethylate, potassium methylate, or potassium ethylate, an alkali metal hydride, for example sodium hydride, or an organic base, for example an alkyl amine such as triethylamine. The reaction may be carried out in a non polar or polar solvent, for example an aromatic hydrocarbon such as benzene, toluene, or xylene, an alkanol having from 1 to 6 carbon atoms, for example methanol or ethanol, an ether, for example dioxane or tetrahydrofurane, or solvents such as diemthylsulfoxide, dimethylformamide or hexamethylphosphortriamide. The reaction can be accelerated or completed by the application of heat, for example by heating to the boiling point of the solvent.

It is a further object of the present invention to provide a process for the preparation of the intermediates of formula III in which X is oxygen and $R^6$ has the above meaning, which comprises alkylating or acylating in known manner a compound of formula III in which X is oxygen and $R^6$ stands for hydrogen.

It is a further object of the present invention to provide a process for the preparation of the intermediates of formula III in which X is sulfur and $R^6$ stands for acyl, which comprises acylating in known manner a compound of formula III in which X is sulfur and $R^6$ stands for hydrogen.

The starting compounds of formula V necessary for the aforesaid processes are prepared by known methods [cf. C.A. 64, 6627, (1966); Hoffmann La Roche & Co. AG., Netherlands Pat. No. 6,401,827, 27th Aug. 1965].

The starting compounds of formula V in which $R^6$ is hydrogen can also be prepared by the following process, which is also an object of the invention, and which comprises treating a compound of formula VI

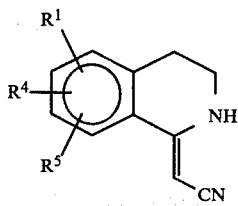

VI in which $R^1$, $R^4$ and $R^5$ have the above meaning with a suitable acid, for example formic acid, trifluoroacetic acid or polyphosphoric acid. The reaction can be accelerated or completed by heating to, for example, 80° to 150° C.

The compounds of formula VI can be prepared by known methods [cf. C.A. 64, 6627, (1966), Hoffmann La Roche & Co. AG, Netherlands Pat. No. 6,401,827, 27th Aug. 1965; K. Harsanyi, K. Takaes, E. Bendeh and A. Neszmelyi, Liebigs Ann. Chem. 1606 (1973)].

It is a further object of the present invention to provide a process for preparing the intermediates of formula III in which X is sulfur, which comprises treating a compound of formula III in which X is oxygen with an inorganic sulfide according to known methods.

It is also a feature of the present invention to provide a process for preparing the intermediates of formula IV in which Y is a halogen, which comprises treating a compound of formula III in which X is oxygen with an inorganic halide by a known method.

The present invention further provides a process for preparing the intermediates of formula IV in which Y is an alkoxy group having at most 6 carbon atoms, which comprises treating a compound of formula IV in which Y stands for a halogen, preferably chlorine, with an alkali metal alcoholate according to a known method.

The intermediates of formula IV in which Y is an alkoxy group having at most 6 carbon atoms may also be prepared by a different process according to which a compound of formula III in which X is oxygen is reacted with a trialkyloxonium fluoroborate, for example triethyloxonium fluoroborate. The reaction may be carried out in the presence of a solvent, for example a halogenated aliphatic hydrocarbon, for example dichloromethane.

It is another object of the invention to provide a process for preparing an intermediate of formula IV in which Y is alkylthio, which comprises treating a compound of formula III in which X is sulfur with an alkyl halide, for example methyl iodide according to a known method.

In the first place the present invention provides a process for preparing pyrimido(6,1-a)isoquinolin-4-one derivatives of formula I and their salts, which comprises reacting a compound of formula III or IV in which $R^1$, $R^4$, $R^5$ and $R^6$ have the meaning as indicated in claim 1 and X stands for sulfur and Y stands for halogen, alkoxy or alkylthio, with a compound of the formula

in which $R^2$ and $R^3$ have the aforesaid meaning, with the exception, however, that they do not represent acyl, in the presence of a base, and treating the free base obtained with an acid to obtain the salt. As a base the compound of the formula

itself can be used which is added in excess of that required for the reaction, or an alkali metal hydride, for example sodium hydride, or a tertiary amine, for example triethyl amine, or an acid acceptor, for example diazobicyclononene. The reaction may be carried out in the presence of polar solvents such as dimethylformamide, dimethylsulfoxide, halogenated aliphatic hydrocarbons, for example chloroform, or alkanols, for example butanol, or in the presence of aprotic solvents such as high boiling ethers such as diethylene glycol dimethyl ether. The reaction may be accelerated or completed by the application of heat, for example by heating to the boiling point of the solvent.

Compounds of the formula I in which either $R^2$ or $R^6$ and $R^3$ represent alkyl, cycloalkyl, substituted alkyl, aralkyl, heterocyclically substituted alkyl and aryl as defined above can be prepared from compounds of formula I in which either $R^2$ or $R^6$ are hydrogen by a treatment, in the presence of a base or of a salt, with a halide of the formula RX in which R has the same meaning as indicated above for $R^2$ and $R^6$. If R is phenyl the phenyl nucleus carries appropriate substituents in order that the halide has a sufficient reactivity. X in formula RX is halogen, for example chlorine, bromine or iodine. Suitable bases are alkali metal carbonates, for example potassium carbonate, alkali metal hydrides, for example sodium hydride, a tertiary amine, such as triethylamine, or an acid scavenger such as diazobicyclononene. Suitable salts are metal fluorides, for example potassium fluoride. The reaction may be carried out in the presence of polar solvents, for example dimethylformamide or dimethylsulfoxide, halogenated aliphatic hydrocarbons such as chloroform, or ketones such as acetone, or in the presence of aprotic solvents, for example high boiling ethers such as diethylene glycol dimethyl ether. The reaction can be accelerated or completed by the application of heat, for example by heating to the boiling point of the solvent. This process is especially suitable for transforming compounds of formula I, in which either $R^2$ or $R^6$ denotes hydrogen and $R^3$ is an aryl radical, into compounds of formula I in which either $R^2$ or $R^6$ denotes alkyl or substituted alkyl and $R^3$ stands for aryl.

The process described in the preceding paragraph may lead to quaternary ammonium salts of the isomers of formula I. Alternatively the free bases of formula I can be transformed separately into quaternary ammonium salts or acid addition salts by known methods.

Compounds of formula I in which $R^2$, $R^3$ or $R^6$ stands for an acyl radical can be prepared from compounds of formula I in which at least one of the radicals $R^2$, $R^3$ or $R^6$ represents hydrogen by a treatment with an acyl halide or acyl anhydride in which the acyl radical is an alkanoyl group having at most 6 carbon atoms, for example acetyl, or an aroyl group, for example benzoyl, in which the phenyl nucleus can be substituted as defined above, and the halogen may be chlorine. The reaction may be carried out in the presence of a base, for example an alkali metal carbonate, such as potassium carbonate, or a tertiary amine, such as triethylamine. The reaction can be accelerated by heating to the boiling point of the acylating agent. The pyrimido(6,1-a)isoquinolin-4-one derivatives of the invention possess valuable pharmacological properties, for example hypotensive, broncho-dilatory and antiallergic acitivity.

Because of their hypotensive activity, the compounds are suitable for the treatment and prevention of heart and circulatory diseases, for example essential and malignant hypertonia, heart insufficiency, Angina pectoris and disturbances of the peripheral circulation. The novel compounds can also be used in combination with other pharmacologically active substances, for example with diuretics, antiarrhythmic agents, β-blockers, tranquilizers, heart vasodilating agents and hypolipidemics.

Because of their bronchodilatory and antiallergic effect, the compounds can be used for the treatment and prevention of diseases of the respiratory system, for example bronchial asthma, chronic bronchitis, emphysema and allergies such as allergic asthma, hay fever, allergic rhinitis and conjunctivitis urticaria etc. The compounds can also be used in combination with other pharmacologically active substances such as corticosteroids, sympathomimetics, xanthine derivatives, antihistamines, tranquilizers, cardiac stimulants etc.

The active substances according to the invention can be administered perorally, parenterally (intramuscularly, intravenously, subcutaneously), rectally, or topically, optionally in the form of an aerosol.

The following doses are used in mammals, particularly man: to reduce the blood pressure: a daily dose of 0.1 to 200 mg, dosage unit 0,1 to 25 mg; as a bronchospasmolytic and antiallergic agent: a daily dose of 1 to 500 mg, dosage unit 1 to 100 mg The compounds can be administered either per se or in admixture with pharmacologically tolerable carrier materials. For oral administration, the active compounds are mixed with the usual substances and transformed into a conventional form for administration, for example tablets, push-fit capsules, aqueous alcoholic or oily suspensions or solutions. Suitable inert carrier materials are, for example, magnesium carbonate, milk sugar or cornstarch, which can be used with the addition of other substances such as magnesium stearate. The compositions can be prepared in the form of dry or moist granules. As oily carriers or solvents, vegetable and animal oils can be used, for example sunflower oil and cod-liver oil.

In emergency situations, the active compounds can be administered intravenously. To this end, the active compounds or the physiologically tolerable salts thereof, as far as they have a sufficient solubility, are dissolved in the usual auxiliaries, which may also act as a dissolving intermediary or buffer.

Physiologically tolerable salts are formed, for example, with the following acids: hydrochloric acid, hydrobromic acid and hydroiodic acid, phosphoric acid, sulfuric acid, methylsulfuric acid, amidosulfonic acid, nitric acid, tartaric acid, lactic acid, malonic acid, fumaric acid, oxalic acid, citric acid, malic acid, mucic acid, benzoic acid, salicylic acid, aceturic acid, embonic acid, naphthalene-1,5-disulfonic acid, ascorbic acid, phenylacetic acid, p-aminosalicylic acid, hydroxyethanesulfonic acid, benzene-sulfonic acid, or synthetic resins containing acid groups, for example those having an ion exchange effect.

Suitable solvents for intravenous administration are, for example, water, physiological sodium chloride solution or dilute alcohols such as ethanol, propanediol or glycerol; furthermore sugar solutions, such as glucose or mannitol solutions, or a mixture of the aforesaid solvents.

The following examples illustrate the invention.

EXAMPLE 1

6,7-Dimethoxy-1-carbamoylmethylene-1,2,3,4-tetrahydroisoquinoline

Polyphosphoric acid (10.0 g) is heated to 100° C. and 1.0 g of 6,7-dimethoxy-1-cyanomethylene-1,2,3,4-tetrahydroisoquinoline is added under mechanical stirring. The reaction mixture is heated for 1 hour, poured into crushed ice and made basic with 30% sodium hydroxide. The mixture is extracted with chloroform and the extract dried over anhydrous sodium sulfate. The solvent is evaporated under reduced pressure to give a white solid, yield 0.7 g, mp. 156°–158° C.

EXAMPLE 2

9,10-Dimethoxy-3,4,6,7-tetrahydro-2H-pyrimido(6,1-a)isoquinolin-2,4-dione

A solution of 6,7-dimethoxy-1-carbamoylmethylene-1,2,3,4-tetrahydroisoquinoline (5.0g) and an excess of sodium ethoxide (prepared from 12.0 g of sodium metal and 600 ml of ethanol) in ethanol is heated. 150.0 ml of diethyl carbonate is added to the solution. The reaction mixture is refluxed for an additional 2.5 hr. The solvent is removed under vacuum and the residue is acidified to give a white precipitate, yield 4.80 g. The product crystallizes from dimethylformamide, mp. 323°–325° C.

EXAMPLE 3

9,10-Dimethoxy-3-methyl-3,4,6,7-tetrahydro-2H-pyrimido-(6,1-a)isoquinolin-2,4-dione A mixture of 9,10-dimethoxy-3,4,6,7-tetrahydro-2H-pyrimido(6,1-a)isoquinolin-2,4-dione (4.11 g), oil-free sodium hydride (0.75 g) and dimethylformamide (100 ml) is heated for 15 minutes to 100° C. and then cooled to room temperature. Methyl iodide (10 ml) is added and the reaction mixture is heated for 12 hours to 100° C. The solvent is removed under reduced pressure and the residue treated with cold water. The solid matter is filtered off and recrystallized from ethyl acetate/methylene chloride. Yield 4.0 g, melting point 260°–262° C.

EXAMPLE 4

9,10-Dimethoxy-3-isopropyl-3,4,6,7-tetrahydro-2H-pyrimido-(6,1-a)isoquinolin-2,4-dione In a manner analogous to that of Example 3, 9,10-dimethoxy-3,4,6,7-tetrahydro-2H-pyrimido(6,1-a)isoquinolin-2,4-dione is reacted with isopropyl iodide. Yield 50%; melting point 190°–192° C.

EXAMPLE 5

9,10-Dimethoxy-2-thio-2,3,6,7-tetrahydro-4H-pyrimido(6,1-a)isoquinolin-4-one A mixture of 9,10-dimethoxy-3,4,6,7-tetrahydro-2H-pyrimido(6,1-a)isoquinolin-2,4-dione (10.0 g) and phosphorus pentasulfide (9.0 g) in 200 ml of pyridine is refluxed for 5 hours. Pyridine is removed under pressure. The residue is treated with dilute hydrochloric acid and then extracted with methylene chloride. The methylene chloride extract is dried over anhydrous sosium sulfate and evaporated to dryness leaving a white powder which is crystallized from chloroform-ether mixture, yield 10.0 g, m.p. 236°–237° C.

EXAMPLE 6

9,10-Dimethoxy-3-methyl-2-thio-2,3,6,7-tetrahydro-4H-pyrimido(6,1-a)isoquinolin-4-one Phosphorus pentasulfide (1.0 g) is added to a solution of 9,10-dimethyl-3-methyl-3,4,6,7-tetrahydro-2H-pyrimido(6,1-a)isoquinolin-2,4-dione (0.5 g) in pyridine (10 ml). The mixture is refluxed for 15 hours, the solvent removed under reduced pressure and the residue repeatedly extracted with methylene chloride. The combined methylene chloride extracts are washed with dilute hydrochloric acid and with water, dried over sodium sulfate and evaporated to dryness. The residue is chromatographed to yield the desired compound. Yield 0.25 g, m.p. 230°–231° C.

EXAMPLE 7

9,10-Dimethoxy-2-chloro-6,7-dihydro-4H-pyrimido(6,1-a)isoquinolin-4-one

A mixture of 30.0 g of 9,10-dimethoxy-3,4,6,7-tetrahydro-2H-pyrimido(6,1-a)isoquinolin-2,4-dione and 300 ml of phosphorus oxychloride is heated on a steam bath for 4 hours. The excess of phosphorus oxychloride is distilled under reduced pressure. The residue is poured into a cold solution of sodium hydroxide. A yellow solid precipitates which is collected by filtration. The product is purified by passage through a silica gel column using chloroform as eluent. Yield 28.0 g, m.p. 235°–236° C.

EXAMPLE 8

9,10-Dimethoxy-2-butoxy-6,7-dihydro-4H-pyrimido(6,1-a)isoquinolin-4-one 1.46 g of 9,10-dimethoxy-6,7-dihydro-2-chloro-4H-pyrimido(6,1-a)isoquinolin-4-one are added to a mixture of 1.0 g of sodium hydroxide and 50.0 ml of n-butanol. The reduction mixture is refluxed for 6 hours. The solvent is removed under reduced pressure. The residue is treated with water and extracted with chloroform. The extract is dried over anhydrous $Na_2SO_4$ and evaporated to give a white solid. After crystallization from a chloroform-ether mixture, 0.7 g of the title compound is obtained, m.p. 158°–159° C.

EXAMPLE 9

9,10-Dimethoxy-2-ethoxy-6,7-dihydro-4H-pyrimido(6,1-a)-isoquinolin-4-one

A mixture of 3.0 g of 9,10-dimethoxy-3,4,6,7-tetrahydro-2H-pyrimido(6,1-a)isoquinolin-2,4-dione and 15.0 g of triethyloxonium fluoroborate in 100 ml of dichloromethane is stirred overnight. The reaction mixture is washed with a solution of sodium carbonate. The organic layer is separated and dried over anhydrous sodium sulfate. Evaporation of the solvent gives the title compound, yield 1.8 g.

EXAMPLE 10

9,10-Dimethoxy-2-methylmercapto-6,7-dihydro-4H-pyrimido(6,1-a)isoquinolin-4-one hydroiodide To a suspension of 10.0 g of 9,10-dimethoxy-2-thio-2,3,6,7-tetrahydro-4H-pyrimido(6,1-a)isoquinolin-4-one in 200 ml of tetrahydrofuran, 20 ml of methyliodide is added and the reaction mixture refluxed for 4 hours. A white solid precipitates and is collected by filtration. It is crystallized from chloroform-methanol mixture, yield 10.50 g, m.p. 220°–225° C. (dec.).

EXAMPLE 11

General procedure for the preparation of compounds of the general formula I from compounds of formula III or IV Compound III (X=S) or any one of the compounds IV (Y=Cl, SCH$_3$, OBu) is heated with an about equimolar amount of the appropriate amine of the general formula HNR$_2$R$_3$. The reaction is carried out in the presence of a base or an acid scavenger. The base is preferably the reacting amine itself, used in excess of that required for the reaction. The reaction is also preferably carried out in the presence of a suitable solvent as defined in the text. The reaction mixture may be heated to refluxing temperatures for 2–10 hours. The solvent is evaporated under reduced pressure. The residue is treated with water and extracted with an organic solvent. The extract is allowed to stand over anhydrous sodium sulfate and evaporated to dryness. The residue is purified by chromatography and/or crystallized to give the desired compound, which, if desired, is converted to its salt.

EXAMPLE 12

9,10-Dimethoxy-2-tert-butylamino-6,7-dihydro-4H-pyrimido(6,1-a)isoquinolin-4-one hydrochloride A solution of 9,10-dimethoxy-2-chloro-6,7-dihydro-4H-pyrimido(6,1-a)isoquinolin-4-one (3.0 g) and tert.-butylamine (10.0 ml) in chloroform (75 ml) is heated under reflux for 16 hours. The solvent is evaporated under reduced pressure and the residue triturated with a dilute solution of sodium hydroxide to give a white precipitate. The precipitate is filtered, dried and converted into its hydrochloride by treating it in solution in ethanol with hydrochloric acid. The hydrochloride is crystallized from ethanol-ether mixture, yield 3.0 g, m.p. 265°–270° C.

EXAMPLE 13

9,10-Dimethoxy-2-sec-butylamino-6,7-dihydro-4H-pyrimido(6,1-a)isoquinolin-4-one hydrochloride A solution of 9,10-dimethoxy-6,7-dihydro-2-chloro-4H-pyrimido(6,1-a)isoquinolin-4-one (2.5 g), sec-butylamine (10 ml) and dimethylformamide (2 ml) is heated under reflux for 5 hours. The solvent and excess amine are distilled under reduced pressure. The residue is treated with water. A white solid precicipitates and is collected by filtration. The precipitate is crystallized from methylene chloride-ether mixture, yield 2.10 g. The crystals are dissolved in dichloromethane and treated with a solution of etheral hydrochloric acid. The hydrochloride is crystallized from ethanol-ether mixture, m.p. 218°–225° C.

EXAMPLE 14

9,10-Dimethoxy-2-(2,6-dimethylanilio)-6,7-dihydro-4H-pyrimido(6,1-a)isoquinolin-4-one A solution of 9,10-dimethoxy-2-chloro-6,7-dihydro-4H-pyrimido(6,1-a)isoquinolin-4-one (2.5 g), 2,6-dimethylaniline (5.0 ml) in butanol (20.0 ml) is heated under reflux for 10 hours. The solvent is evaporated under reduced pressure to give a gummy mass. Chromatography of the gummy mass over silica gel using benzene-ethyl acetate as the eluant gives the required product. The compound is crystallized from methanol, yield 2.0 g, m.p. 297°–299° C.

EXAMPLE 15

9,10-Dimethoxy-2-(2,4-dimethylanilino)-6,7-dihydro-4H-pyrimido(6,1-a)isoquinolin-4-one The procedure described in Example 14 is followed by using 2,4-dimethylaniline in place of 2,6-dimethylaniline. Yield: 75%, m.p. 239°–241° C.

EXAMPLE 16

9,10-Dimethoxy-2-(2-chloroanilino)-6,7-dihydro-4H-pyrimido(6,1-a)isoquinolin-4-one hydrochloride monohydrate The procedure described in Example 14 is followed, using 2-chloroaniline in place of 2,6-dimethylaniline. The hydrochloride is prepared as described in Example 12. Yield 70%, m.p. 182°–186° C.

EXAMPLE 17

9,10-Dimethoxy-2-(2,4,6-trimethylanilino)-6,7-dihydro-4H-pyrimido(6,1-a)isoquinolin-4-one hydrochloride dihydrate The procedure described in Example 14 is followed using 2,4,6-trimethylaniline in place of 2,6-dimethylaniline. The hydrochloride is prepared as described in Example 12. Yield 70%, m.p. 167°–169° C.

EXAMPLE 18

9,10-Dimethoxy-3-methyl-2-mesitylimino-2,3,6,7-tetrahydro-4H-pyrimido(6,1-a)isoquinolin-4-one A mixture of 9,10-dimethoxy-3-methyl-2-thio-2,3,6,7-tetrahydro-4H-pyrimido(6,1-a)isoquinolin-4-one (0.1 g) and methyl iodide (2 ml) in tetrahydrofurane (10 ml) is refluxed for 2 hours. The solid matter is filtered off and heated for 3 hours to 100° to 110° C. together with 2,4,6-trimethylaniline (0.4 g). The excess trimethylaniline is removed by treating the reaction mixture with petroleum ether. The residue is worked up to give the desired compound, which is recrystallized from ethyl acetate/petroleum ether. Yield 80 mg; m.p. 151°–152° C.

The same compound can also be obtained by direct reaction of 9,10-dimethoxy-3-methyl-2-thio-2,3,6,7-tetrahydro-4H-pyrimido(6,1-a)isoquinolin-4-one with 2,4,6-trimethylaniline.

EXAMPLE 19

9.10-Dimethoxy-3-methyl-2-n-butylimino-2,3,6,7-tetrahydro-4H-pyrimido(6,1-a)isoquinolin-4-one In a manner analogous to that of Example 18, the compound is prepared from 9,10-dimethoxy-3-methyl-2-thio-3,4,6,7-tetrahydro-4H-pyrimido(6,1-a)isoquinolin-4-one and n-butylamine. Yield 100%, m.p. 120°–121° C.

EXAMPLE 20

General procedure for the preparation of compounds of the formula I from compounds of formulae Ia and Ib The compound of formula Ia or Ib, in which $R^3$ preferably represents aryl, is reacted in the presence of a base, an acid scavenger, or a salt, with a halide of the formula $R^2X$ or $R^6X$. The halide can be used in equimolar amounts or in an excess. The reaction is preferably carried out in the presence of a solvent as defined above. The reaction mixture may be refluxed for 2 to 50 hours. The solvent is evaporated under reduced pressure. The residue is treated with water and extracted with an organic solvent. The extract is dried over anhydrous sodium sulfate and the filtrate is evaporated to dryness. The residue is purified by chromatography and/or recrystallized to give the desired compound which can be transformed into its salt, if desired.

EXAMPLE 21

(a)

9,10-Dimethoxy-3-methyl-2-mesitylimino-2,3,6,7-tetrahydro-4H-pyrimido(6,1-a)isoquinolin-4-one, its hydrochloride and methiodide and (b)

9,10-Dimethoxy-2-(N-methyl-2,4,6-trimethylanilino)-6,7-dihydro-4H-pyrimido(6,1-a)isoquinolin-4-one and its hydrochloride A suspension of 9,10-dimethoxy-2-(2,4,6-trimethylanilino)-6,7-dihydro-4H-pyrimido(6,1-a)isoquinolin-4-one (3.0 g) anhydrous potassium carbonate (15.0 g) and methyl iodide (45.0 ml) in acetone (300.0 ml) is heated under reflux for 15 hours. The reaction mixture is cooled and filtered. The filtrate is concentrated under reduced pressure, whereby a residue is obtained. Chromatography of the residue over silica gel using benzene-chloroform (1:1) as the eluant gives the desired free bases (a) 2.3 g, m.p. 151°–152° C. and (b) 0.15 g, m.p.

175°–176° C. Further elution of the chromatography column with chloroform gives 0.35 g of the methiodide of base (a) of m.p. 221°–222° C. The hydrochlorides are prepared from the bases by the procedure described in Example 13. They are crystallized from dichloromethane/petroleum ether (b.p. 60°–80° C.) or dichloromethane/ethyl acetate or ethanol/diethyl ether. M.p. of hydrochloride (a) 198°–200° C., m.p. of hydrochloride (b) 189°–191° C.

EXAMPLE 22

(a)
9,10-Dimethoxy-2-(N-isopropyl-2,4,6-trimethylanilino)-6,7-dihydro-4H-pyrimido(6,1-a)isoquinolin-4-one and (b)
9,10-dimethoxy-3-isopropyl-2-mesitylimino-2,3,6,7-tetrahydro-4H-pyrimido(6,1-a)isoquinolin-4-one 9,10-Dimethoxy-2-(2,4,6-trimethylanilino)-6,7-dihydro-4H-pyrimido(6,1-a)isoquinolin-4one (5.85 g) and dimethylformamide (30 ml) are added to oil-free sodium hydride (1.5 g). The mixture is heated for 5 minutes to 110° C. and then cooled to room temperature. Isopropyl iodide (2.55 g) is added and the whole is heated to 110° C. for 40 hours. After cooling, methanol is added to the reaction mixture and the solvents are removed under reduced pressure. The residue is extracted with chloroform, the extract washed with water, dried over sodium sulfate and evaporated to dryness. The residue is chromatographed to give the bases (a) m.p. 182°–183° C. and (b) m.p. 178°–179° C.

EXAMPLE 23

(a)
9,10-Dimethoxy-2-(N-ethyl-2,4,6-trimethylanilino)-6,7-dihydro-4H-pyrimido(6,1-a)isoquinolin-4-one and (b)
9,10-dimethoxy-3-ethyl-2-mesitylimino-2,3,6,7-tetrahydro-4H-pyrimido(6,1-a)isoquinolin-4-one Procedure A:
Example 21 is repeated with the exception that ethyl iodide is used instead of methyl iodide.

Procedure B:
9,10-Dimethoxy-2-(2,4,6-trimethylanilino)-6,7-dihydro-4H-pyrimido(6,1-a)isoquinolin-4-one (0.5 g) and potassium fluoride (0.5 g) are added to dimethylformamide (10 ml). The mixture is heated to 100° C. for 1 hour and then cooled. Ethyl iodide (0.2 g) is added and the whole is heated to 100° C. for 40 hours. The solvent is removed under reduced pressure and the residue worked up as described in Example 22.

The procedures A and B yield the two isomers in different proportions. Free base (a) m.p. 164°–165° C.; free base (b) m.p. 142°–143° C.

EXAMPLE 24

9,10-dimethoxy-2-(N-acetyl-2,4,6-trimethylanilino)-6,7-dihydro-4H-pyrimido-(6,1-a)isoquinolin-4one 1.2 ml of triethylamine are added first to an ice-cold solution of 9,10-dimethoxy-2-(2,4,6-trimethyl-anilino)-6,7-dihydro-4H-pyrimido(6,1-a)isoquinolin-4-one (1.6 g) in chloroform (40.0 ml), and then a solution of acetyl chloride (0.64 ml) in chloroform (10.0 ml) is added dropwise. The mixture is stirred for 2 hours. The chloroform solution is washed successively with water, sodium carbonate solution and water, and is then dried over anhydrous sodium sulfate. The solution is filtered and the filtrate evaporated to dryness in vacuo. The residue is triturated with diethyl ether to yield the desired compound in solid form. Yield 1.6 g, m.p. 210°–212° C. (dichloromethane-petroleum ether b.p. 60°–80° C.).

What is claimed is:

1. A compound of the formula

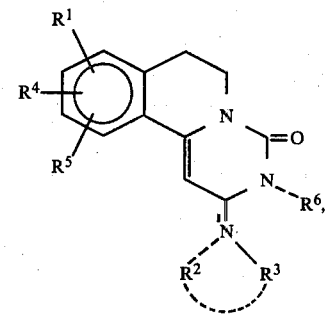

an acid addition salt thereof with an inorganic or organic acid, or a quaternary ammonium salt thereof formed by reaction with an alkyl halide,
wherein
$R^1$, $R^4$, and $R^5$, taken alone, are the same or different and are hydrogen, $C_1$–$C_3$ alkoxy, $C_1$–$C_6$ alkanoyloxy, or halogen, or
any two of $R^1$, $R^4$ and $R^5$, in adjacent positions and taken together, are methylenedioxy or ethylenedioxy;
$R^2$ and $R^3$, taken alone, are the same or different and are hydrogen, hydroxy, amino, $C_1$–$C_6$ alkyl substituted by furyl or tetra-hydrofuryl, $C_1$–$C_6$ alkyl, $C_1$–$C_6$ hydroxyalkyl, di($C_1$–$C_3$ alkoxy) $C_1$–$C_6$ alkyl, halo-$C_1$–$C_6$ alkyl, di($C_1$–$C_4$ alkyl)amino $C_1$–$C_6$ alkyl, phenyl-$C_1$–$C_2$ alkyl, or phenyl-$C_1$–$C_2$ alkyl wherein the phenyl is mono-, di-, or tri-substituted with $C_1$–$C_3$ alkoxy, $C_1$–$C_6$ alkanoyl, unsubstituted phenyl or by phenyl mono- or poly-substituted with $C_1$–$C_3$ alkoxy, $C_1$–$C_3$ alkyl, halogen, or trifluoromethyl, or
$R^2$ and $R^3$, taken together with the nitrogen atom to which they are attached, are morpholino or piperizino or morpholino or piperizino substituted with $C_1$–$C_6$ alkyl, piperidino, phenyl, or phenyl substituted with $C_1$–$C_3$ alkoxy or by tri-fluoromethyl; and
$R^6$ is hydrogen, $C_1$–$C_6$ alkyl, di-($C_1$–$C_4$ alkyl) amino-$C_1$–$C_6$ alkyl, or di-($C_1$–$C_6$ alkyl)-phosphinyl-$C_1$–$C_3$ alkyl; but
if $R^6$ is defined as above, then $R^2$ represents an electron pair and if $R^2$ is defined as above, then $R^6$ represents an electron pair.

2. 9,10-Dimethoxy-2-tert.-butylamino-6,7-dihydro-4H-pyrimido(6,1-a)isoquinoline-4-one hydrochloride.

3. 9,10-Dimethoxy-2-(2,4,6-trimethylanilino)-6,7-dihydro-4H-pyrimido(6,1-a)isoquinolin-4-one hydrochloride dihydrate.

4. 9,10-Dimethoxy-3-methyl-2-mesitylimino-2,3,6,7-tetrahydro-4H-pyrimido(6,1-a)isoquinolin-4-one hydrochloride.

5. 9,10-Dimethoxy-2-(N-methyl-2,4,6-trimethylanilino)-6,7-dihydro-4H-pyrimido(6,1-a)isoquinolin-4-one hydrochloride.

6. 9,10-Dimethoxy-3-isopropyl-2-mesitylimino-2,3,6,7-tetrahydro-4H-pyrimido(6,1-a)isoquinolin-4-one hydrochloride.

7. 9,10-Dimethoxy-2-(N-isopropyl-2,4,6-trimethylanilino)-6,7-dihydro-4H-pyrimido(6,1-a)isoquinolin-4-one hydrochloride.

8. 9,10-Dimethoxy-3-ethyl-2-mesitylimino-2,3,6,7-tetrahydro-4H-pyrimido(6,1-a)isoquinolin-4-one hydrochloride.

9. 9,10-Dimethoxy-2-(N-ethyl-2,4,6-trimethylanilino)-6,7-dihydro-4H-pyrimido(6,1-a)isoquinolin-4-one hydrochloride.

10. 9,10-Dimethoxy-3-acetyl-2-mesitylimino-2,3,6,7-tetrahydro-4H-pyrimido(6,1-a)isoquinolin-4-one.

11. 9,10-Dimethoxy-2-(N-acetyl-2,4,6-trimethylanilino)-6,7-dihydro-4H-pyrimido(6,1-a)isoquinolin-4-one.

12. A pharmaceutical composition for the treatment of hypertonia, bronchospasms, or allergies, which composition comprises a pharmaceutically effective amount of a compound as in claim 1 and a pharmaceutically acceptable excipient.

13. A method for the treatment of hypertonia, bronchospasms, or allergies in a mammal suffering therefrom, which method comprises orally, parenterally, rectally, or topically administering to said mammal a pharmaceutically effective amount of a compound as in claim 1.

* * * * *

UNITED STATES PATENT AND TRADEMARK OFFICE
CERTIFICATE OF CORRECTION

PATENT NO. : 4482556

DATED : November 13, 1984

INVENTOR(S) : Lal et al.

It is certified that error appears in the above-identified patent and that said Letters Patent is hereby corrected as shown below:

Column 1, lines 35-47 and Column 30, lines 10-20 (in claim 1)) change  "   "   To  --   --

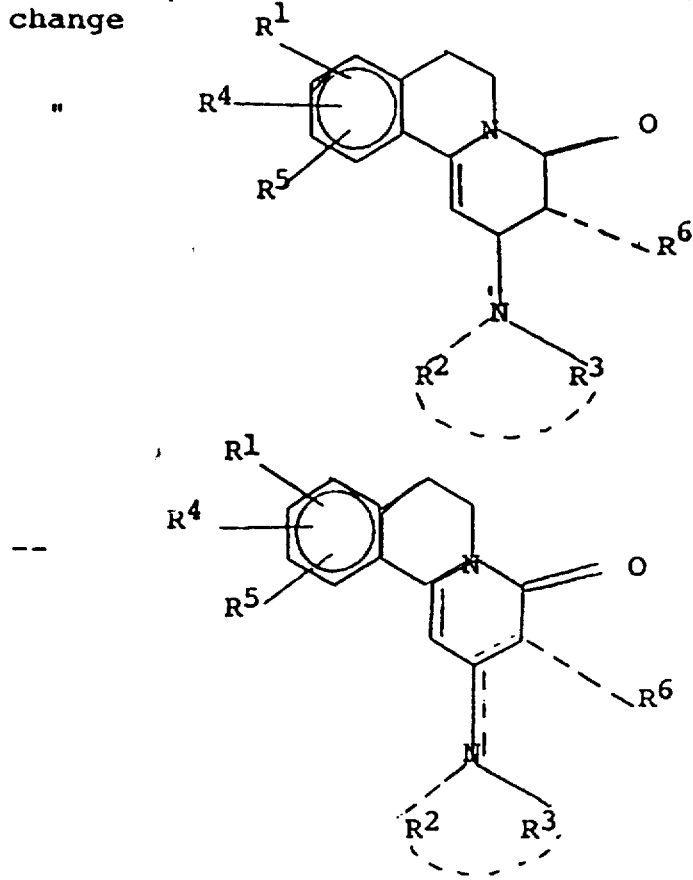

UNITED STATES PATENT AND TRADEMARK OFFICE
CERTIFICATE OF CORRECTION

PATENT NO. : 4,482,556

DATED : November 13, 1984

INVENTOR(S) : Lal et al.

It is certified that error appears in the above-identified patent and that said Letters Patent is hereby corrected as shown below:

Column 30, line 44 (in claim 1, each occurrence), change "piperizino" to --piperazino--

Signed and Sealed this

Twenty-fifth Day of June 1985

[SEAL]

Attest:

DONALD J. QUIGG

Attesting Officer

Acting Commissioner of Patents and Trademarks